US011147677B2

(12) United States Patent
Persaud

(10) Patent No.: US 11,147,677 B2
(45) Date of Patent: Oct. 19, 2021

(54) ARTIFICIAL MENISCUS

(71) Applicant: Philip A. Persaud, Glen Mills, PA (US)

(72) Inventor: Philip A. Persaud, Glen Mills, PA (US)

( * ) Notice: Subject to any disclaimer, the term of this patent is extended or adjusted under 35 U.S.C. 154(b) by 0 days.

(21) Appl. No.: 15/406,788

(22) Filed: Jan. 16, 2017

(65) Prior Publication Data

US 2017/0202672 A1    Jul. 20, 2017

Related U.S. Application Data

(60) Provisional application No. 62/279,722, filed on Jan. 16, 2016.

(51) Int. Cl.
| | | |
|---|---|---|
| *A61F 2/38* | (2006.01) |
| *A61L 27/54* | (2006.01) |
| *A61L 27/18* | (2006.01) |
| *A61F 2/30* | (2006.01) |
| *A61L 27/48* | (2006.01) |

(52) U.S. Cl.
CPC ........ *A61F 2/3872* (2013.01); *A61F 2/30942* (2013.01); *A61L 27/18* (2013.01); *A61L 27/48* (2013.01); *A61L 27/54* (2013.01); *A61F 2/30965* (2013.01); *A61F 2002/30065* (2013.01); *A61F 2002/3093* (2013.01); *A61F 2002/30677* (2013.01); *A61F 2002/30957* (2013.01); *A61F 2002/30962* (2013.01); *A61F 2002/30985* (2013.01); *A61F 2310/00359* (2013.01); *A61F 2310/00365* (2013.01); *A61L 2300/414* (2013.01); *A61L 2430/06* (2013.01)

(58) Field of Classification Search
CPC ................ A61F 2/3872; A61F 2/30965; A61F 2002/30985; A61F 2002/30065; A61F 2002/3093; A61F 2002/30957; A61L 27/54; A61L 2430/06; A61L 2300/414
See application file for complete search history.

(56) References Cited

U.S. PATENT DOCUMENTS

| | | | | |
|---|---|---|---|---|
| 5,451,351 A | * | 9/1995 | Blackmore | ......... B29C 63/0069 138/97 |
| 2009/0259314 A1 | * | 10/2009 | Linder-Ganz | ......... A61F 2/3872 623/14.12 |

(Continued)

OTHER PUBLICATIONS

3D-Printed Implant Infused with Human Growth Factors Regenerates Meniscus, AZO Materials, Oct. 30, 2015.

(Continued)

*Primary Examiner* — Bruce E Snow
*Assistant Examiner* — Melissa A Hoban
(74) *Attorney, Agent, or Firm* — Michael S. Young; Michael S. Young IP Law LLC

(57) ABSTRACT

An artificial meniscus using a thermoplastic for the base material, which is reinforced with an inert material. In a preferred embodiment, the reinforcement is provided by Kevlar® fibers, and the matrix is made out of polycarbonate-urethane (PCU). In an alternate embodiment, the PCU can also be surrounded by a polycaprolactone (PCL) scaffold that is infused with human growth proteins so that when the artificial meniscus is implanted, stem cells in the body are stimulated to ensure the meniscus is properly secured.

12 Claims, 4 Drawing Sheets

(56) References Cited

U.S. PATENT DOCUMENTS

| | | | | |
|---|---|---|---|---|
| 2010/0256777 | A1* | 10/2010 | Datta | A61L 27/18 |
| | | | | 623/23.72 |
| 2013/0079877 | A1* | 3/2013 | Buma | A61F 2/3872 |
| | | | | 623/14.12 |
| 2013/0312897 | A1* | 11/2013 | Vowles | A61B 17/0401 |
| | | | | 156/83 |
| 2017/0007411 | A1* | 1/2017 | Khan | A61F 2/389 |

OTHER PUBLICATIONS

Meniscus Structure in Human, Sheep, and Rabbit for Animal Models of Meniscus Repair, by Anik Chevrier, et al., Wiley InterScience (www.interscience.wiley.com) Feb. 25, 2009.

Protein-Releasing Polymeric Scaffolds Induce Fibrochondrocytic Differentiation of Endogenous Cells for Knee Meniscus Regeneration in Sheep, by Chang H. Lee, Scott A. Rodeo, Lisa Ann Fortier, Chuanyong Lu, Cevat Erisken and Jeremy J. Mao, Science Translation Medicine, Dec. 10, 2014, vol. 6, Issue 266.

Elsner, JJ, et al., Design Optimization of a Polycarbonate-Urethane Meniscal Implant in the Sheep Knee, Jul. 15, 2013, Post. No. 1057, 56th Ann Meet Orthopaedic Research Soc.

\* cited by examiner

ARTIFICIAL MENISCUS

CLAIM FOR PRIORITY

The subject application claims priority under all applicable U.S. statutes, including 35 U.S.C. § 119(e), to U.S. Provisional Application No. 62/279,722, filed Jan. 16, 2016, titled Improved Artificial Meniscus.

FIELD OF THE INVENTION

The subject invention relates to knee implants and, more specifically, the manufacture of an artificial human meniscus made of reinforced polycarbonate-urethane (PCU).

BACKGROUND OF THE INVENTION

A number of animal joints contain at least one fibrocartilaginous structure for separating a joint cavity known as a meniscus. For example, the human knee comprises bones (the femur, tibia and fibula), ligaments, cartilage, and two menisci. In addition to the knee, humans have menisci in their jaws, shoulders, clavicles and wrists. (It is also known that some animals have more menisci than humans) A meniscus divides a joint cavity for the purpose of reducing friction between bones, dispersing force, and facilitating the movement of bone over bone.

The two menisci in the human knee are found on the medial and lateral sides of the knee and are known as the medial meniscus and the lateral meniscus. The menisci in the human knee are crescent-shaped cartilages that separate the femur from the tibia. Both menisci in the human knee are concave on their top surfaces, and are relatively flat on their bottom surfaces.

Both of the knee menisci serve as gliding surfaces that prevent the femur from grinding into the tibia. Although a knee can function without one or both menisci, an injury to a meniscus can be extremely painful and can lead to debilitating arthritis in the knee joint.

There are generally two types of injuries to the medial and lateral knee menisci—acute tears and chronic tears. Acute tears will sometimes heal themselves through rest, but usually require surgery since there is limited blood flow to the menisci. Surgery for an acute tear usually involves trimming the frayed edge of the meniscus, and/or trephination which induces bleeding to aid repair. Chronic tears require a partial or complete meniscectomy. Surgical intervention is required in approximately 85% of all cases of meniscal injuries.

Although a patient who has had a partial or complete meniscectomy can usually continue with their day-to-day activities, heavier use, as is encountered in sporting activities or physical labor, is best avoided. The reason heavier activity should be avoided is that the removal of the meniscus almost always results in an accelerated deterioration of the knee joint and early onset of osteoarthritis.

Accordingly, doctors and researchers are striving to develop a meniscus transplant that can adequately replace and mimic the original meniscus before it was damaged. An early attempt to solve the problem was to transplant a meniscus that was removed from a cadaver. However, the availability of cadavers, and the difficulty in finding a cadaver meniscus of the right size and shape, have limited this option as a viable solution. As is evident to one skilled in the art, there is a need for artificial menisci. Therefore, orthopedic surgeons and researchers are racing to develop an artificial, replacement meniscus that can be inserted after a complete meniscectomy.

Research in the field of artificial human knee meniscus has been conducted for almost two decades. It is known that menisci in sheep are similar to human knee menisci. Accordingly, research on sheep menisci for repair/replacement is common in this orthopaedic field. See "Meniscus Structure in Human, Sheep, and Rabbit for Animal Models of Meniscus Repair" by Anik Chevrier, et al., Wiley InterScience (www.interscience.wiley.com) 25 Feb. 2009, and "Protein-Releasing Polymeric Scaffolds Induce Fibrochondrocytic Differentiation of Endogenous Cells for Knee Meniscus Regeneration in Sheep" by, Chang H. Lee, Scott A. Rodeo, Lisa Ann Fortier, Chuanyong Lu, Cevat Erisken and Jeremy J. Mao, Journal of Orthopaedic Research, September 2009. It is hoped that the research on sheep menisci will lead to a break-through that will apply to the design and manufacture of an artificial human meniscus.

In the research conducted by a team led by Dr. Jeremy J. Mao, a meniscus scaffold is printed using a 3D printer and polycaprolactone (PCL) material. See also "Protein-Releasing Polymeric Scaffolds Induce Fibrochondrocytic Differentiation of Endogenous Cells for Knee Meniscus Regeneration in Sheep," by Mao, J. J., et al., Sci Transl Med 2014. Polycaprolactone is used in the manufacture of surgical sutures. The Mao scaffold meniscus is infused with protein growth factors. This has the two-fold benefit of increasing the likelihood of attachment and protecting against rejection, thus allowing surrounding tissue to attach and secure the artificial meniscus.

The protein growth factors include transforming growth factor β3 (TGFβ3) and connective growth factor (CTGF), recombinant human proteins. These two recombinant human proteins were delivered sequentially. After the protein infused meniscus is manufactured, the damaged meniscus is removed and the scaffold is inserted in its place. Analysis of sheep knees, in which Dr. Mao's meniscus scaffold replaced the original meniscus, showed that the protein infused scaffold attracted stem cells in the body that induced the sheep's body to create new meniscal tissue forming a bond around the artificial meniscus.

An isotropic approach is being explored by an Israeli company that has designed a replacement meniscus utilizing polyethelene reinforced polycarbonate urethane (PCU). See "Design Optimization of a Polycarbonate-Urethane Meniscal Implant in the Sheep Knee" by Elsner, J J; Zur, G.; Guilak, F.; et al.; Poster 1057, 56th Annual Meeting of the Orthopaedic Research Society. The reason for using PCU is that it is Food and Drug Administration (FDA) approved, and this would be a significant benefit when it comes to seeking approval for use in humans.

Replacement menisci made completely of PCU proved limited in distributing pressure at the bone-on-bone impact points. Accordingly, J J Elsner's team infused the PCU with reinforcement fibers circumferentially around the outer periphery of the PCU meniscus. Testing showed that pressure distribution improved significantly but was not able to fully mimic the weight distribution efficiency of a human meniscus. J J Elsner's team used Kevlar® for the reinforcement fibers. Since the combination of Kevlar® and PCU has been shown to increase pressure distribution throughout the artificial meniscus, J J Elsner's team continues testing with these two materials.

Early research in the field of artificial replacement menisci has been promising, and testing is ongoing, but a viable solution has not been found. Accordingly, there is thus a growing need for new methods of treating meniscus injuries in humans and, in particular, the manufacture of replacement menisci for the human knee.

SUMMARY OF THE INVENTION

An artificial meniscus in accordance with the present invention comprises a polycarbonate-urethane resin reinforced by an inert fiber/fabric (such as Kevlar®) that is distributed throughout the resin. This reinforcement can be a quasi-isotropic layup in the form of a braid, multiple plies of fabric, or discontinuous short fibers.

The fiber reinforcement exists throughout the entire structure of the artificial meniscus. In the preferred embodiment, polycarbonate-urethane (PCU) is used as the resin and Kevlar® is used for the fiber reinforcement.

Another embodiment of the subject invention includes the use of polycaprolactone (PCL) scaffold that surrounds the reinforced PCU meniscus.

Yet another embodiment will include the aforementioned PCL scaffold that surrounds the PCU meniscus and which is infused with recombinant human growth factor proteins.

The subject invention also includes the manufacturing process. A two-piece split mold is manufactured by a 3D printer using the mirror image of data taken from an MRI of the patient's healthy meniscus. After manufacturing the two-piece mold, the next step of manufacturing the artificial meniscus is substantially identical to typical compression molding techniques. The PCU resin and the synthetic reinforcement fibers are placed in the two-piece mold cavity. After the two-piece mold is closed, heat and pressure are applied to fabricate the artificial meniscus (which is in the shape of a healthy meniscus before it was damaged). The PCL scaffold is then applied by using another 3D printer.

The subject invention may take on a number of embodiments to achieve the aforementioned purposes.

DETAILED DESCRIPTION OF THE PREFERRED EMBODIMENT

Figure 1:
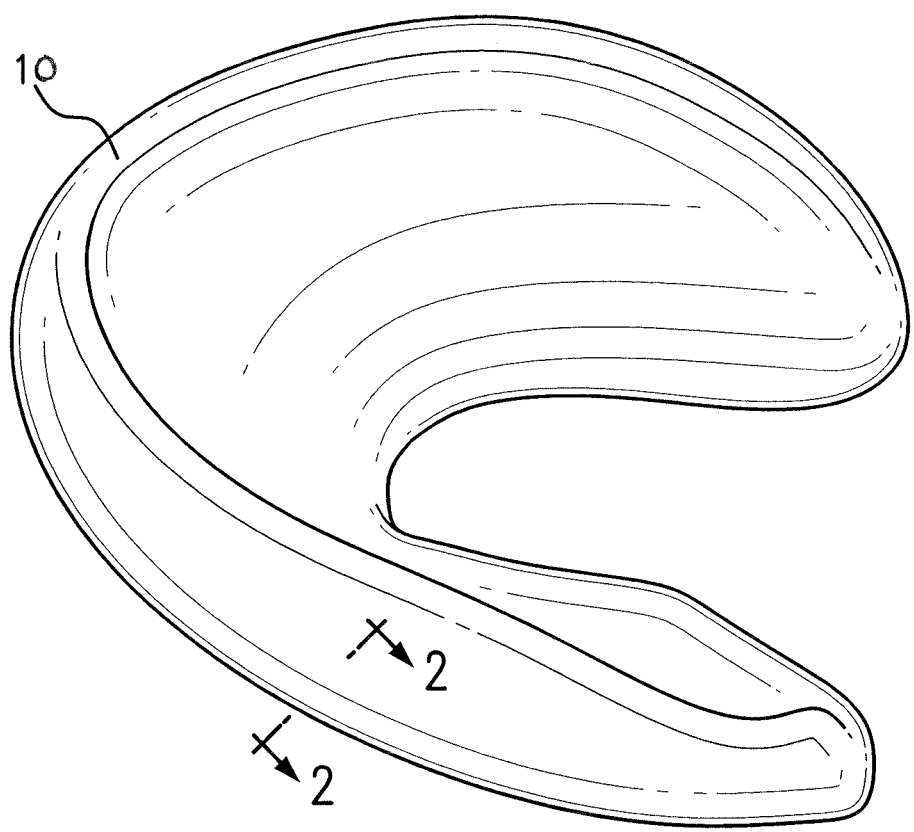
FIG. 1 is a perspective view of an artificial, human, lateral meniscus in accordance with the present invention.

The subject invention is a polycarbonate-urethane reinforced composite (PaRC) artificial meniscus. The PaRC described and claimed herein is designed to fully replace a human meniscus. Referring to FIG. 1, a perspective view of a polycarbonate-urethane reinforced composite (PaRC) artificial human meniscus 10 manufactured in accordance with the present invention is shown. The subject invention includes: A) a reinforced artificial meniscus; B) a reinforced artificial meniscus having a bio-polymer scaffold; C) a reinforced artificial meniscus having a polymer scaffold in which the scaffold is infused with recombinant human proteins; and D) a process of manufacturing said reinforced meniscus.

Figure 5:
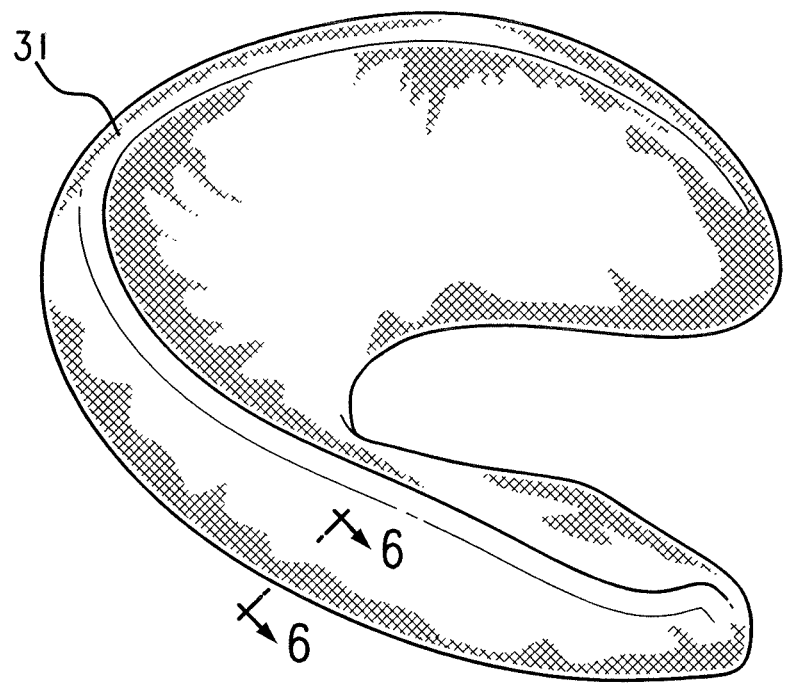
FIG. 5 is a perspective view of the protein scaffold of the artificial human meniscus shown in FIG. 1.

Referring again to FIG. 1, in a preferred embodiment, the meniscus 10 is made of reinforced polycarbonate-urethane (PCU). The reinforcement comprises one or more plies of synthetic fiber/fabric that are added to the PCU during the manufacturing process. In a preferred embodiment, the synthetic fiber is Kevlar®. This fiber reinforcement can be a quasi-isotropic layup in the form of a braid, multiple plies of fabric, or discontinuous short fibers. The PCU meniscus of FIG. 1 is surrounded with a polycaprolactone (PCL) scaffold 31 as illustrated in FIG. 5. In the preferred embodiment, the scaffold is a two-piece shell. In another embodiment, the PCL scaffold is infused with recombinant human proteins as will be disclosed below.

Figure 2:
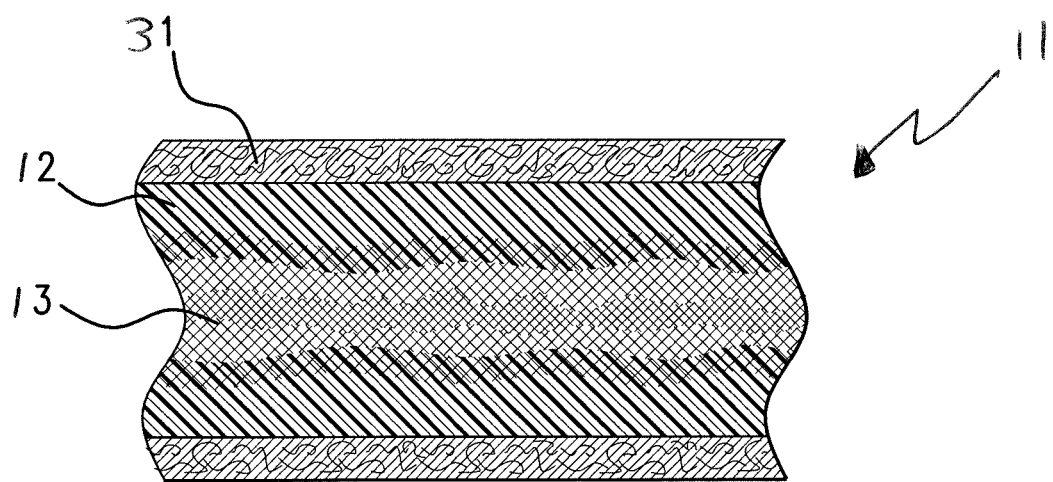
FIG. 2 is a cross-sectional view of the artificial meniscus of FIG. 1 taken along line 2-2.

As illustrated in FIG. 1, the subject meniscus 10 is made from a composite core 11 and encased in a protein scaffold 31. FIG. 2 is a cutaway view of the meniscus shown in FIG. 1 taken along lines 2-2. The protein scaffold 12 is integrated into the composite core 11.

Figure 3:
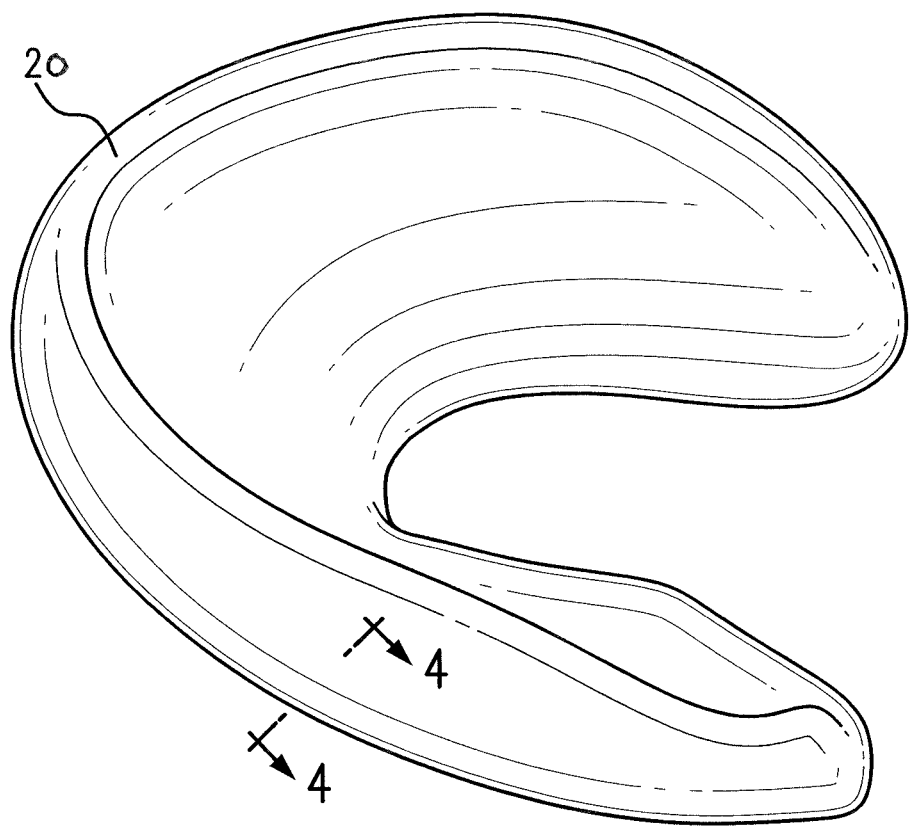
FIG. 3 is a perspective view of only the cartilage scaffold of the artificial human meniscus shown in FIG. 1.
Figure 4:
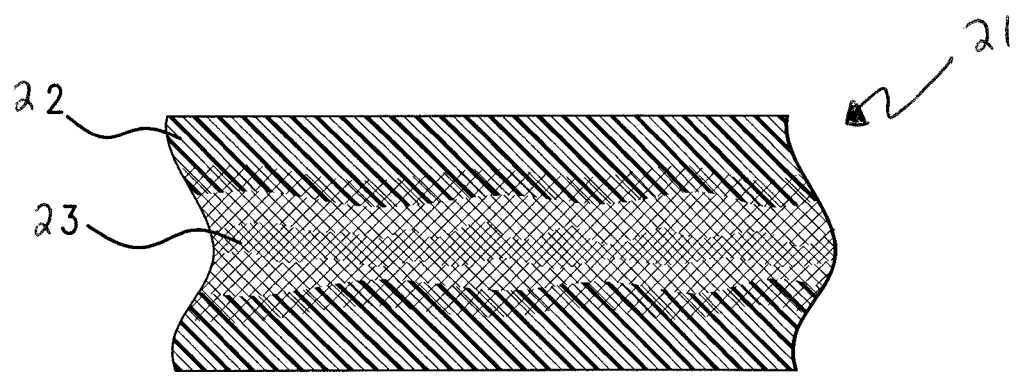
FIG. 4 is a cross-sectional view of the artificial meniscus of FIG. 3 taken along line 4-4.

FIGS. 3 and 4 illustrate the composite core of the artificial meniscus shown in FIG. 1. (FIGS. 3 and 4 can also illustrate a less expensive embodiment in which the reinforced artificial meniscus 20 does not include a scaffold.) The composite core 21 of the subject meniscus 20 is made out of a polycarbonate-urethane (PCU) resin 22 reinforced with synthetic fibers (e.g., Kevlar®) 23 as illustrated in FIG. 4 which is a cross-sectional view taken along line 4-4 of FIG. 3. The synthetic fibers 23 are preferably concentrated in the middle of the meniscus 20 but are spread throughout the entire composite.

The synthetic fibers 23 should be bio-inert, and are included to increase the overall properties of the PCU resin 22 including helping to distribute load throughout the composite core 21. The combination of PCU resin 22 and synthetic fibers 23 is designed to increase the durability and maximum load capabilities of the PaRC meniscus, allowing it to be a viable option for meniscal replacement in high-load bearing patients such as athletes. However, even non-athletes will benefit from the subject invention especially patients who must perform strenuous physical activity in their day-to-day jobs.

Figure 6:
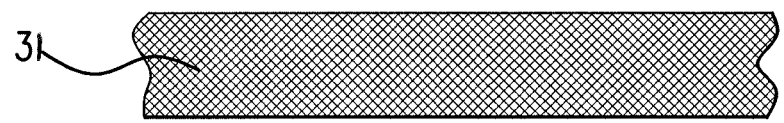
FIG. 6 is a cross-sectional view of the protein scaffold of FIG. 5 taken along line 6-6.

Referring to FIGS. 5 and 6, the protein scaffold 31 of the subject invention is illustrated. In this embodiment, the composite core of the artificial meniscus 10 is completely surrounded with a protein scaffold 31. In its base configuration, the protein scaffold consists only of a biodegradable polymer, preferably polycaprolactone.

In another embodiment, the protein scaffold 31 is infused with recombinant human proteins of β3 (TGFβ3) and connective growth factor (CTGF). The recombinant human proteins β3 (TGFβ3) and connective growth factor (CTGF) are infused into the protein scaffold to promote cellular growth around the composite core. This allows the PaRC meniscus to be secured by the patient's tendons, rather than being screwed into the tibia, resulting in decreased recovery time and reducing the possibility of rejection.

The subject invention includes the meniscus manufacturing process. Before a patient's damaged meniscus is removed, an MRI scan is taken in situ of the patient's healthy meniscus in the non-injured knee and a three-dimensional (3D) interpretation is made. If the patient does not have a healthy meniscus from which a model can be manufactured, then a model made from another patient (preferably with a similar body size and type) can be substituted. Over a period of time, a library of 3D models (or MRI data) from various patients will be developed and can be used when an MRI scan cannot be taken from a new patient (e.g., when both the left and right knees' menisci of the new patient are damaged or deteriorated to such a point that the MRI data cannot be used to make a mold).

Dr. Mao's team takes the data from the 3D model then communicates it to a 3D printer to manufacture a meniscus scaffold. The scaffold will be an anatomically correct copy (substantially the same size and shape) of the patient's meniscus before it was injured. The J J Elsner research team makes a 3D model from the MRI scan.

The previously-mentioned articles—"Protein-Releasing polymeric scaffolds induce fibrochondrocytic differentiation of endogenous cells for knee meniscus regeneration in sheep," by Mao, J. J., et al., and "Design Optimization of a Polycarbonate-Urethane Meniscal Implant in the Sheep Knee," by Elsner, J J; et al.,—are incorporated by reference as if fully set forth herein.

In contrast with both Dr. Mao's and J J Elsner's methods, the present invention uses the data from the MRI to fabricate a two-piece, split mold using a 3D printer. The artificial meniscus manufactured in accordance with the present invention will be made using a compression molded process.

Generally speaking, in compression molding, the molding material is first placed in an open mold cavity. After the mold is closed, heat and pressure are applied to force the material into contact with the entire interior surface area of the mold. Heat and pressure are maintained until the molding material has taken the complete form of the mold, and then it is cooled until cured.

With respect to the subject invention, after manufacturing the two-piece split mold, the next step of manufacturing the artificial meniscus of FIG. 1 is substantially identical to typical compression molding techniques. The mold is filled with the desired ratios of synthetic fiber and PCU, closed, heated under pressure and then allowed to cool. Once the meniscus has cured, the fabricated artificial meniscus is in the shape of an undamaged human meniscus.

In the present invention, the mold used to make the artificial meniscus of FIG. 1 is preferably manufactured in accordance with data taken by an MRI scan of the patient's healthy meniscus (i.e., from the opposite knee's meniscus that was not injured and is not being replaced). Specifically, the mold is made of the mirror image of the MRI data of the opposite knee's meniscus; therefore, the compression molded meniscus should be a close match to the pre-injury meniscus.

Prior to closing the mold, the synthetic fiber 13 and PCU 12 are placed within the two-piece mold. Heat and pressure are applied to ensure that the PCU is forced into contact with the entire interior surface of the mold. Once the mold is allowed to cool, it is opened and the artificial meniscus is removed. In this manner, the reinforcing fiber 13 is distributed throughout the entire structure of the artificial meniscus 10. (In contrast to the process of J J Elsner's team using reinforced fibers only on the periphery of the meniscal implant.)

Referring again to FIG. 3, in the preferred embodiment, polycarbonate-urethane (PCU) 22 is used as the resin to make the artificial meniscus 20. Polycarbonate-urethane (PCU) is used in the preferred embodiment for several reasons, including the known quality of being compatible with human tissue. In addition, PCU is designed to mimic human cartilage in hardness, as well cartilage's extracellular matrix and density. PCU also has high abrasion resistance, flexibility, and tensile strength. PCU has been tested rigorously by the FDA and has been approved for use in human medical implants. However, as would be clear to a person skilled in the art, other resins may be substituted for PCU, especially resins that are being tested but have not yet been approved by the FDA for use in human implants.

Once the artificial meniscus 10 (or 20) has cured, it is reinforced throughout its entire structure by the synthetic fiber. In the two primary embodiments (i.e., the embodiments illustrated in FIGS. 1 and 3), the position(s) of the synthetic fiber 13 (or 23) within the PCU are illustrated in cross-sectional views shown in FIGS. 2 and 4. As indicated previously, it is preferred that the fibers and the PCU are loaded in the two-piece mold such that the fibers are distributed throughout the base but concentrated in the center of the meniscus.

In the preferred embodiment, Kevlar® is used as the synthetic fiber 13. See FIGS. 1 through 4. Kevlar® was selected as the reinforcing material in the preferred embodiment because of its high strength-to-weight ratio and because of its inert characteristics, therefore making it compatible with human tissue. In addition, the Kevlar® fiber used to reinforce the resin and to aid in weight distribution mimics the fibroblastic properties that are present in collagen, which make up the matrix of a natural human meniscus. However, a person skilled in the art may substitute other bio-inert material(s) as the reinforcing fiber.

The synthetic fibers 13 (or 23) can be in the form of a braided fabric, woven fabric, or short, discontinuous fibers. The three forms of the synthetic fibers were chosen due to their ability in other applications to provide a quasi-isotropic layup. The synthetic fiber reinforcement (especially Kevlar®) will permit the PaRC meniscus to disperse energy over the entire meniscal structure in order to provide increased tensile strength and abrasion resistance which allows for increased durability. The reinforcement is throughout the entire structure of the artificial meniscus (and preferably concentrated in the center) as previous studies found the peripheral reinforcement was not adequate.

Currently, a range of 15%-25% of Kevlar® reinforcement by weight is believed to be adequate in any of the three primary embodiments (braid, multiple plies of fabric, or discontinuous short fibers). However, additional research and testing may reveal that another percentage range by weight of fiber reinforcement in the artificial meniscus will further optimize the physical and mechanical properties of the human meniscus.

Referring again to FIGS. 1, 2, 5 and 6, the subject invention may include a polycaprolactone (PCL) scaffold 31 which surrounds the reinforced artificial meniscus. The PCL scaffold can be manufactured using a similar three dimensional protein process disclosed by Dr. Mao. Dr. Mao's method disclosed two PCL halves joined together on the PCU meniscus using BioGlue®. In contrast to Dr. Mao's technique, the subject invention uses a 3D printer to apply the PCL scaffold to the exterior of the meniscus. (See FIG. 2.)

Although the preferred embodiment includes the PCL scaffold, the subject meniscus illustrated in FIGS. 3 and 4, without the scaffold, may be acceptable in certain situations such as when the patient is not an athlete and the meniscus will not be subject to high-load bearing activities.

In yet another embodiment, the polycaprolactone (PCL) scaffold of FIGS. 1, 2, 5 and 6 may be infused with human growth proteins so that when the artificial meniscus is implanted, stem cells in the body are stimulated to ensure the meniscus is properly secured. Protein growth factors, such as transforming growth factor β3 (TGFβ3) and connective growth factor (CTGF), recombinant human proteins, are added to the PCL scaffold which surrounds the reinforced artificial PCU meniscus 10. The human growth proteins stimulate stem cells in the body in order to create new cartilage tissue that helps surrounding knee tissue to bond to the artificial meniscus. After the artificial meniscus is implanted and the knee heals, the PCL scaffold will dissolve and is subsequently replaced with cartilage.

Figure 7:
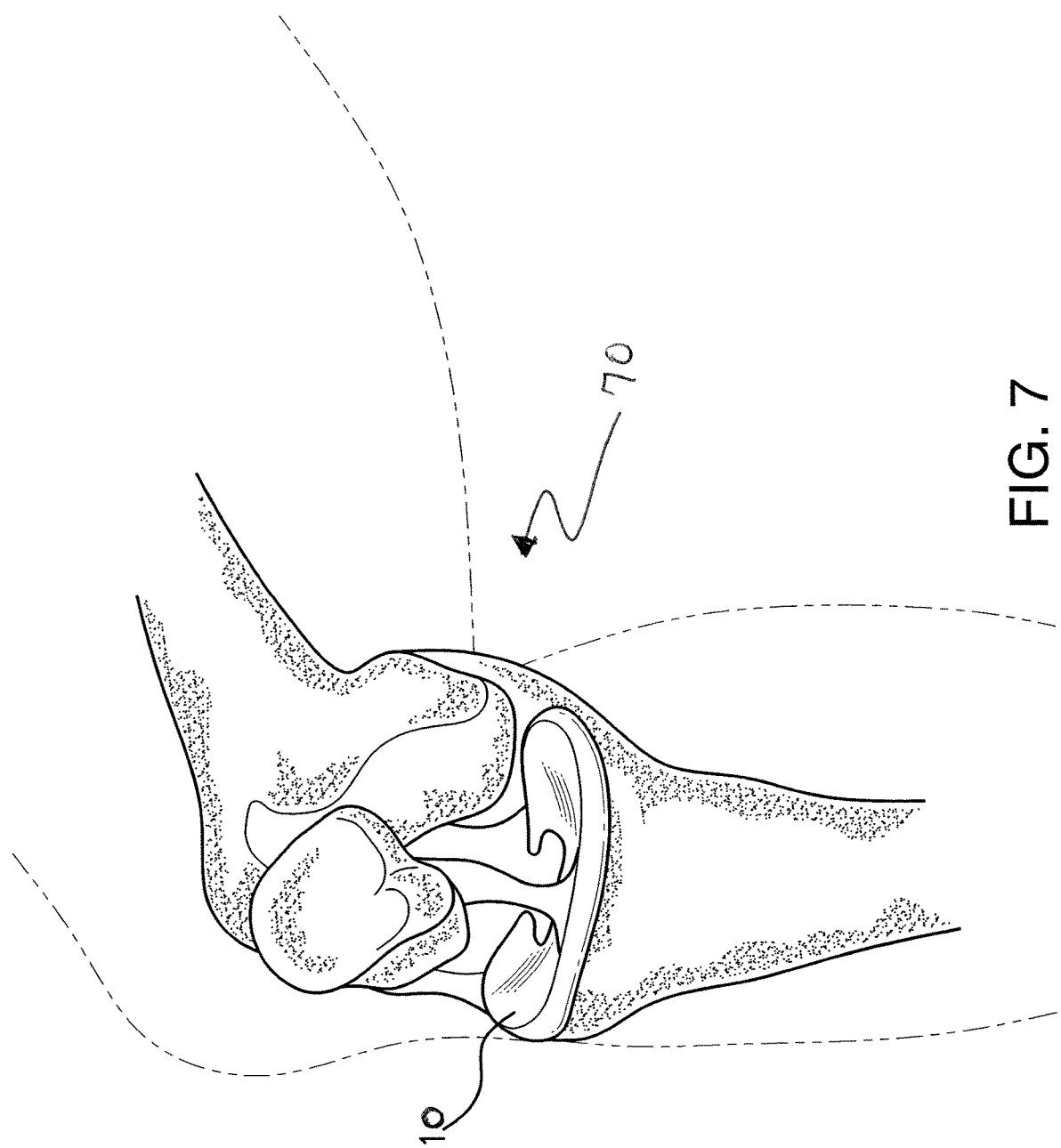
FIG. 7 is a view of a human knee showing the placement of the artificial, lateral meniscus of FIG. 1.

Referring to FIG. 7, the artificial meniscus 10 in accordance with the present invention is shown in position within a human knee 70. Each human knee has two menisci—lateral and medial. The subject invention can be used to replace either one of the menisci or both menisci. (If only one meniscus in one knee is replaced with the subject invention, it can be safely used in conjunction with the remaining natural meniscus.)

The PCL scaffold 31 is used in the primary embodiments of the subject synthetic fiber reinforced artificial meniscus. Referring again to FIG. 1, the polycaprolactone (PCL) scaffold 31 is to be 3D printed onto the surface of the reinforced PCU after its fabrication and cure, and before the meniscus is to be implanted.

In computer simulations, the combination of PCU reinforced with Kevlar® fibers has been predicted to exceed the capabilities of current mensical prosthetics of pure resin design by up to 30%. Furthermore, current meniscal prosthetics are not designed for long-term use or extensive weight-bearing activities, making them unsuitable to be used as a replacement meniscus for athletes. Not only does the subject PaRC meniscus disclosed herein address these two issues, it significantly reduces recovery time.

The meniscus implant made in accordance with the subject disclosure is designed to fully replace a human meniscus, and prevent, or at least slow, the development of arthritis in the knee joint. Moreover, it is designed to provide a safe and quick recovery from meniscal surgery, and allow for full range of motion and weight-bearing capabilities before the natural human meniscus was damaged.

It should be noted that the subject disclosure is aimed at a human meniscus. However, one skilled in the art can modify the manufacturing technique (primarily making the mold) to manufacture an animal (e.g., sheep, monkey, elephant, etc.) meniscus. It should be noted that an animal meniscus may not have the same constraints of manufacturing a human meniscus since the FDA does not need to approve most animal implants.

Although this invention has been described and illustrated by reference to specific embodiments, it will be apparent to those skilled in the art that various changes, modifications and equivalents may be made which clearly fall within the scope of this invention. The present invention is intended to be protected broadly. Insofar as the description above and the accompanying drawings disclose any additional subject matter that is not within the scope of the claims below, the inventions are not dedicated to the public and the right to file one or more applications to claim such additional inventions is reserved.

I claim:

1. An apparatus comprising:
   a resin;
   a synthetic fiber reinforcement within the resin is configured to form a synthetic fiber reinforced artificial replacement meniscus; and
   a scaffold that encases the synthetic fiber reinforced artificial replacement meniscus.

2. The apparatus of claim 1, wherein the resin is a polycarbonate-urethane resin.

3. The apparatus of claim 1, wherein the synthetic fiber reinforcement is Kevlar.

4. The apparatus of claim 1, wherein the synthetic fiber reinforcement is configured to provide a quasi-isotropic layup.

5. The apparatus of claim 1, wherein the scaffold is configured to dissolve and be replaced with cartilage after the synthetic fiber reinforced artificial replacement meniscus is implanted.

6. The apparatus of claim 1, wherein the scaffold is infused with transforming growth factor β3 (TGFβ3) and connective growth factor (CTGF).

7. The apparatus of claim 1, wherein the synthetic fiber reinforcement exists throughout an entire structure of the synthetic fiber reinforced artificial replacement meniscus.

8. An apparatus comprising:
   a resin;
   a synthetic fiber reinforcement within the resin is configured to form a synthetic fiber reinforced artificial replacement meniscus, wherein the synthetic fiber reinforcement is a bio-inert material; and
   a bio-polymer scaffold that encases the synthetic fiber reinforced artificial replacement meniscus.

9. The apparatus of claim 8, wherein the synthetic fiber reinforced artificial replacement meniscus is configured to be secured by surrounding knee tissue of a patient.

10. The apparatus of claim 8, wherein the bio-polymer scaffold consists only of a biodegradable polymer configured to dissolve and be replaced with cartilage after the synthetic fiber reinforced artificial replacement meniscus is implanted, so that the synthetic fiber reinforced artificial replacement meniscus fully replaces a human meniscus.

11. The apparatus of claim 10, wherein the biodegradable polymer is polycaprolactone.

12. The apparatus of claim 8, wherein the bio-polymer scaffold is infused with transforming growth factor β3 (TGFβ3) and connective growth factor (CTGF).

* * * * *